United States Patent [19]

Faunce

[11] 4,198,394

[45] Apr. 15, 1980

[54] SODIUM DIHYDROGEN PHOSPHATE ENHANCED DENTIFRICE COMPOSITION

[76] Inventor: Frank R. Faunce, 201 Wilcrest Dr., #946, Houston, Tex. 77042

[21] Appl. No.: 11,134

[22] Filed: Feb. 12, 1979

Related U.S. Application Data

[63] Continuation-in-part of Ser. No. 927,846, Jul. 25, 1978.

[51] Int. Cl.$^2$ .............................................. A61K 7/18
[52] U.S. Cl. ........................................ 424/52; 424/57
[58] Field of Search ..................................... 424/52, 57

[56] References Cited

U.S. PATENT DOCUMENTS

| | | | |
|---|---|---|---|
| 1,471,987 | 10/1926 | Vogt | 424/57 |
| 1,691,504 | 11/1928 | Vogt | 424/57 |
| 2,069,157 | 1/1937 | Sahyun | 424/57 |
| 2,876,166 | 3/1959 | Nebergall | 424/52 |
| 2,876,167 | 3/1959 | Manahan | 424/52 |
| 3,105,013 | 9/1963 | Saul et al. | 424/52 |
| 3,282,792 | 11/1966 | Fiscella | 424/52 |
| 3,462,366 | 8/1969 | Luoma | 424/57 |

*Primary Examiner*—Shep K. Rose
*Attorney, Agent, or Firm*—James L. Jackson

[57] ABSTRACT

A sodium dihydrogen phosphate stannous fluoride containing dentifrice composition wherein the enamel penetration and effectiveness of the fluoride is enhanced by sodium dihydrogen phosphate causing the enamel crystalline latticework of the teeth to become activated and allowing the stannous fluoride to penetrate and remain in the tooth enamel for a sufficient period of time to render the enamel effectively resistant to the development of dental caries. The dentifrice also may include a carrier incorporating quantities of abrasive material for polishing, a sweetening agent, a flavoring agent and a foaming agent. Within the acid pH range of between 2 and 5 and preferably 3.5, the sodium dihydrogen phosphate compound alters the crystalline latticework of the enamel thus rendering it capable of inducing deep penetration of fluoride ions and, subsequent to fluoride penetration, a surface capping effect or sealing effect is developed by the stannous fluoride phosphate complex that is effectively resistant to the natural leaching effect of the oral fluids.

8 Claims, No Drawings

SODIUM DIHYDROGEN PHOSPHATE ENHANCED DENTIFRICE COMPOSITION

This application is a continuation-in-part of application Ser. No. 927,846 of Frank R. Faunce, filed July 25, 1978 and entitled DENTIFRICE WITH TOPICAL AND SYSTEMIC PHOSPHATE FLUORIDE SYSTEM.

FIELD OF THE INVENTION

This invention relates generally to dentifrice materials incorporating sodium dihydrogen phosphate for developing caries resistant tooth enamel and dentifrice compositions incorporating a system of fluoride treatment and, more specifically, concerns a dentifrice composition incorporating a quantity of sodium dihydrogen phosphate sufficient to cause substantial enhancement of the caries resistance typically afforded by stannous fluoride. Even more specifically, the present invention concerns the provision of a water free gel or paste carrier of pleasing appearance that incorporates stannous fluoride as the fluoride compound and sodium dihydrogen phosphate as the acid phosphate compound, in such proportions as to render the caries resistant quality of the stannous fluoride substantially more effective than if utilized in the absence of the acid phosphate compound.

BACKGROUND OF THE INVENTION

Topical fluoride treatment with fluoride solutions has been found quite effective in the prevention of dental caries. The most effective type of fluoride treatment is almost always conducted in a clinical environment because of the strong concentration of the fluoride solution that is applied to the teeth. Of course, clinical treatment of this nature severely limits access by the general public to this character of fluoride treatment. Accordingly, dentifrice preparations have been developed and marketed having low concentrations of various fluoride compounds and these preparations have gained widespread acceptance by the public. The anticaries effectiveness of dentifrice products has been materially enhanced by the development of anticaries agents, such as stannous fluoride, sodium monofluorophosphate sodium fluoride, etc. These anticaries agents, when incorporated in dentifrice products, provide topical fluoride treatment with daily dental hygiene. Tests have shown marked reduction in the occurrence of dental caries when the dentifrice utilized for daily dental hygiene includes a fluoride containing compound.

It is desirable to enhance the effectiveness of fluoride compounds, especially stannous fluoride, for caries prevention without necessitating an increase in the concentration of the fluoride compounds in dentifrice products that are available to the general public. For example, it has been found that a concentration of stannous fluoride in the range of 0.3%–0.5%, and preferably 0.4%, of a dentifrice composition yield good results from the standpoint of anticaries treatment. Increasing the concentration of fluoride compound in a dentifrice materially above the level of 0.4% may yield minimal increase in anticaries activity, but the risk of harmful concentrations becomes a matter for careful consideration. For that reason, it is desirable to maintain a concentration of a fluoride compound at about 0.4% of a dentifrice composition and to provide for an increase in the anticaries activity of the product by other suitable means.

The enamel of the teeth is defined by a crystalline latticework of hydroxy-apatite that is effectively resistant to absorption of most materials that are ordinarily present in the oral environment. Fluoride containing dentifrice materials are capable of penetrating the crystalline latticework to a limited degree and therefore fluoride treatment of the teeth is effective for caries resistance only under circumstances where the solution applied to the teeth includes a strong concentration of fluoride. For example, prophylactic pastes and gels utliized in dental offices contain fluoride at about 10% solution. The maximum allowable fluoride concentration in dentifrice materials sold to the public is about 0.4% solution and the fluoride effectiveness is therefore quite limited. It is desirable to provide a fluoride containing dentifrice material that is capable of accomplishing increased fluoride enhanced caries resistance without requiring concentration of fluoride in excess of 0.4% solution.

It is well known that fluoride penetrating the outer surface portion of the crystalline latticework of the enamel tends to leach out quite rapidly. The leaching action begins as soon as the oral cavity is rinsed after brushing, removing the fluoro chemical environment introduced by the dentifrice. It is desirable first to accomplish opening or activation of the crystalline latticework of the enamel and then to provide a surface sealing or capping effect for the enamel to retard the normal leaching action of the oral fluid which would otherwise allow rapid dissipation of the fluoride from the enamel. This activity will allow the fluoride to be retained deeply within the latticework as long as possible so as to provide long term anticaries activity even though fluoride is utilized at or below the weak solution range allowed by governmental authority.

Most dentifrice preparations have a pH in the neutral, slightly basic or slightly acid range. For example, known dentifrice materials having an acid pH do not exceed an acid pH of about 5. The primary reason for this is that decalcification begins to occur in the acid pH range and, since the enamel is eroded to some extent by the abrasive material during the brushing or scrubbing action of oral hygiene it is considered undesirable to cause further deterioration of the enamel by decalcification. It has been determined, however, that the enamel crystalline latticework begins to open or become active at an acid pH and tests indicate that crystalline latticework is able to accept deeper penetration of the fluoride as the latticework opens or becomes activated. Thus, it is desirable to accomplish opening or activation of the crystalline latticework by means of an acid pH to promote deep penetration of the fluoride into the crystalline latticework of the enamel without involving a pH significantly low that decalcification becomes a problem.

In some cases it will not be desirable to utilize a fluoride for daily anticaries activity. In this limited case it is desirable to provide a dentifrice composition that is capable of reacting with the enamel to develop caries resistance.

One of the important aspects of providing a dentifrice that has wide public acceptance is the appearance of the dentifrice material itself. Dentifrice material having a translucent, pleasantly colored appearance is, therefore, a desirable feature insofar as the material also provides optimum prevention of caries and is pleasing to the taste.

Accordingly, it is a primary feature of the present invention to provide a novel dentifrice material that incorporates a fluoride compound for fluoride induced anticaries treatment of the teeth and further incorporates an acid phosphate compound that functions to enhance the anticaries prevention capability of the fluoride compound, without increasing the concentration of the fluoride compound in the dentifrice composition beyond the level of concentration allowed by governmental authority.

It is also a feature of this invention to provide a novel dentifrice composition that incorporates a sufficient quantity of sodium dihydrogen phosphate to alter the crystalline latticework of the enamel causing material enhancement of the resistance of tooth enamel to the development of dental caries.

It is a further feature of this invention to provide a novel dentifrice material which incorporates a sufficient quantity of sodium dihydrogen phosphate to alter the crystalline latticework of the enamel to render the enamel actively receptive to deep penetration of fluoride ions into the crystalline latticework.

Among the several features of the invention is noted the contemplation of a novel dentifrice composition having an acid pH range within which deep penetration of fluoride ions is induced and a subsequent stannous capping effect is developed that effectively prevents leaching of the fluoride or phosphate ions from the enamel of the teeth.

It is also a feature of this invention to provide a novel dentifrice composition incorporating sodium dihydrogen phosphate which reacts with the enamel structure of the teeth to develop an electrically stable fluorophosphate complex within the enamel that promotes long term stability of the caries inhibiting effect of stannous fluoride incorporated therewith.

It is also a feature of the present invention to provide a novel dentifrice material that incorporates stannous fluoride as the fluoride compound, with sodium dihydrogen phosphate as the acid phosphate compound, the resulting combination of the stannous fluoride and acid phosphate causing enhanced fluoride treatment effectiveness of the stannous fluoride.

It is another feature of this invention to provide a novel dentifrice material incorporating a fluoride compound and an acid phosphate compound in a water free gel carrier in order to prevent degradation of the fluoride compound.

It is an even further feature of the present invention to provide a novel dentifrice composition wherein stannous fluoride and sodium dihydrogen phosphate are combined in substantially equal proportions by volume and, at which proportional combination, provide a dentifrice wherein the anticaries effectiveness of the fluoride and the phosphate compounds are materially enhanced.

Another feature of this invention concerns the provision of a novel sodium dihydrogen phosphate containing dentifrice wherein the pH of the resulting dentifrice is in the range of between 2 and 5 and preferably about 3.5.

It is also a feature of this invention to provide a novel fluoride containing dentifrice material that is of pleasing appearance in that it is in the form of a pleasingly colored translucent gel.

It is also a feature of this invention to provide a dentifrice composition incorporating sodium dihydrogen phosphate in sufficient amount to alter the crystalline structure of the enemel and rendering such enamel resistant to caries.

Another feature of this invention concerns the provision of stannous fluoride containing dentifrice material that may be provided with a water-free gel carrier for effective use in single tube delivery systems, or, as an alternative, may be provided in a water containing carrier when double tube delivery systems are to be employed.

Other and further objects, features and advantages of this invention will become obvious to one skilled in the art upon an understanding of the illustrative embodiments about to be described, and various advantages, not referred to herein, will occur to one skilled in the art upon employment of the invention in practice.

SUMMARY OF THE INVENTION

In one form of the invention, a dentifrice composition is provided which incorporates in a water-free carrier a quantity of stannous fluoride compound having a concentration in said dentifrice in the range of from about 0.03% to about 0.5% by weight. For enhancement of the anticaries effectiveness of the fluoride containing compound, the composition also incorporates sodium dihydrogen phosphate, in proportional amounts by volume that render the pH of the dentifrice composition in the range from about 2 to about 5 and preferably about 3.5. The acid phosphate compound may preferably be of substantially equal proportions to the fluoride compound by volume when incorporated into the dentifrice material. Where the dentifrice material is to be incorporated into a single tube delivery system, a pleasingly colored, translucent, water-free gel carrier may be employed as the basic carrier for the dentifrice composition. The carrier may be in the form of a water free paste or gel if stannous fluoride is included. Other conventional dentifrice agents such as binders, abrasive materials, sweeteners, flavoring materials and foaming materials are also incorporated into the dentifrice to provide the various desired functions thereof.

In the alternative, the acid phosphate compound, such as sodium dihydrogen phosphate, may be provided in a water-containing gel or paste carrier where a double compartment delivery tube system is employed. It is imperative that the fluoride containing compound, such as stannous fluoride, for example, be contained within a water-free carrier to prevent rapid ionization and oxidation thereof. An aqueous base may be employed only under circumstances where contact between the water and stannous fluoride cannot occur until the time of application in the oral environment. Where a water-free gel or paste carrier is employed, ionization of the stannous fluoride component is not initiated until contacted by the water of the saliva in the oral environment. Ionization of the stannous fluoride is completed in a period of a few minutes thereafter, but brushing of the teeth typically requires only one or two minutes time during which the topical anticaries treatment of the stannous fluoride compound is effectively manifested. By employing a two tube or two compartmented tube delivery system, the acid phosphate compound and the fluoride containing compound are brought into contact only at the time of delivery. Admixture of these compounds occurs only during brushing and therefore degradation of the fluoride containing compound is initiated only at the time of brushing.

While the present invention is discussed herein primarily from the standpoint of the stannous fluoride and sodium dihydrogen phosphate constituents of the dentifrice composition, it is intended to be understood that in every case the dentifrice composition will also contain other desirable ingredients. For example, at least one of many available sweetening and flavoring agents will be employed as well as one of many suitable and commercially available abrasive agents for effective cleaning and polishing of the teeth. The present invention is discussed herein primarily as it relates to stannous fluoride and sodium dihydrogen phosphate as combined anticaries constituents. Although other fluoride compounds are enchanced to a degree by incorporation of sodium dihydrogen phosphate and other acid phosphates therewith, the enhancement of such fluoride compounds is minimal as compared to the caries resistance enhancement accomplished by appropriate combination of stannous fluoride and sodium dihydrogen phosphate.

Briefly, preferred dentifrice compositions according to this invention comprise a caries inhibiting quantity of stannous fluoride, and a fluoride treatment enhancing quantity of sodium dihydrogen phosphate. Preferably, both the stannous fluoride compound and the sodium dihydrogen phosphate compound are dispersed in a carrier, which may be the same or different carrier as described elsewhere herein, it being necessary only that a water free carrier be employed when the dentifrice composition incorporates stannous fluoride. The stannous fluoride compound and the sodium dihydrogen phosphate compound are provided in such proportions that the pH of the resulting dentifrice composition is between 2 and 5, and preferably about 3.5. It has been determined that combination of stannous fluoride and sodium dihydrogen phosphate at approximately equal volumes in the dentifrice composition will yield a pH of approximately 3.5 and will result in optimum anticaries effectiveness of the resulting dentifrice composition. As used herein, the term "caries inhibiting quantity" means an amount of fluoride compound or acid phosphate compound and specifically sodium dihydrogen phosphate which inhibits or otherwise retards or eliminates the formation of caries in teeth. The term "fluoride enhancing quantity of sodium dihydrogen phosphate" means the quantity of acid phosphate compound that is capable of enhancing the tooth impregnating capacity of the stannous fluoride compound.

The amount of sodium dihydrogen phosphate compound employed is preferably the same as the fluoride compound on a weight percentage basis, however, the amount of acid phosphate may reasonably vary more or less than the fluoride compound as is desired.

The dentifrice material will also incorporate various inert materials that form the gel or paste carrier composition. The specific constituents of the various materials incorporated in each dentifrice composition will be set forth herein in conjunction with the various examples. Percentages are by weight unless otherwise specified.

DETAILED DESCRIPTION OF PREFERRED EMBODIMENT

An example of a dentifrice material that embodies the present invention is identified by the following ingredients and within the limits by weight as set forth below.
Fluoride component—Stannous fluoride: 0.03–0.5%
Binder—Sodium carboxymethylcellulose: 10–75%
Carrier—Glycerin: 5–50%
Sweetening agent—Xylitol: 0.01–5%
Flavoring agent—Spearmint oil: 0.01–5%
Abrasive—Insoluble sodium metaphosphate: 10–75%
Fluoride Enhancement—Sodium dihydrogen phosphate: 0.1–10%
Foaming agent—Sodium lauryl sulfate: 1–10%

The fluoride containing compound utilized is stannous fluoride in the range of from about 0.03% to 0.5% of the composition by weight.

Where detergent materials are employed, such detergents may conveniently take the form identified in U.S. Pat. No. 3,970,747. Other detergents such as sodium lauryl sulfate may also be employed within the spirit and scope of this invention.

The abrasive agent employed in the following examples is insoluble sodium metaphosphate. If translucence is desired, the insoluble sodium metaphosphate will have been pre-treated by tumbling to remove the sharp edges and corners of the crystalline particulate. This pre-treatment modifies the abrasive crystals to render the abrasive refractive rather than reflective, and thus promote the development of a translucent rather than opaque dentifrice gel. Other abrasive materials of light refractive crystalline form may also be utilized. For example, calcium pyrophosphate, bentonite, tricalcium phosphate and sodium aluminum silicate are only a few of the numerous abrasive materials that may be employed in accordance with the teachings of the invention.

The preferred sweetening agent utilized is xylitol which provides a cooling effect in the oral cavity, as well as a humectant capability to retard drying, thus preventing the orifice of the tube from being easily plugged by hardened dentifrice. Other sweetening agents, such as saccharin, or natural sweetening agents, such as honey, may also be employed.

The carrier in the examples is defined primarily by glycerin and a gelling agent such as carboxymethylcellulose. Other gelling agents, such as natural and synthetic gums and gum-like materials such as gum tragacanth, gum acacia, gelatin, sodium alginate, methyl cellulose, polyvinyl-pyrrolidone and the like may also be employed.

The flavoring agent utilized in the examples is spearmint oil and cherry, but other flavoring agents may also be employed. Various artificial or natural flavoring agents are considered acceptable for the dentifrice composition. To provide a dentifrice material that is especially acceptable for use by children, various other fruit flavors, i.e. orange, lemon, lime, pineapple, cherry, etc. may be utilized, as well as chocolate. For adult dentifrice flavors, a mint taste, such as provided by spearmint oil, is considered practical.

Stannous fluoride concentration may vary from about 0.03% to about 0.5%, but at ranges in excess of 0.4% care should be exercised to insure against the development of undesirable systemic effects. It is generally believed the fluoride concentrations exceeding 0.5% should be utilized only under prescription and under professional care and guidance.

The sodium dihydrogen phosphate concentration is sufficient to establish the desired pH range of from about 2 to about 5 and preferably about 3.5. At a pH of about 3.5 the volume of sodium dihydrogen phosphate will substantially equal the volume of the stannous fluoride.

The following specific examples are further illustrative of the nature of the present invention, but it is to be understood that the invention is not limited thereto. The amounts and proportions in the examples are by weight, unless otherwise specified.

EXAMPLE I

Into a container was added 7.5 grams sodium carboxymethylcellulose and 145.0 grams glycerin. The container was slowly heated to 105° F. accompanied by continuous stirring. Stirring in a vacuum environment is preferable, if translucence is desired, to prevent incorporation of air bubbles within the gel. 1.5 grams of xylitol and 2.0 grams of spearmint oil flavoring agent and 0.5 grams coloring agent were added. 2.0 Grams of stannous fluoride, 1,400 grams insoluble sodium metaphosphate and 14.0 grams sodium dihydrogen phosphate and 5.0 grams sodium lauryl sulfate were added during stirring as the container was allowed to cool. The resulting dentifrice composition was in the form of a pleasantly colored blue-green translucent gel.

The general appearance of the product thus produced is pleasant and the product is also pleasant to the taste. When the teeth of the user are brushed with the dentifrice composition identified above, the taste is pleasant during use and a minty pleasant aftertaste remains in the oral cavity of the user for several minutes thereafter. In order to insure optimum fluoride absorption by the teeth of the user, the above composition was provided with equally measured volumes of stannous fluoride and sodium dihydrogen phosphate constituents at 0.4% of the dentifrice composition.

The dentifrice composition of Example I was prepared in several embodiments through variation of the volume of sodium dihydrogen phospate and fluoride penetration tests were conducted on extracted human teeth. The tests indicated that as the pH of the dentifrice composition approaches basic or between 5 and 7, the fluoride penetration becomes minimal. As the pH becomes very acid, i.e. about 2 or greater, fluoride penetration is slightly increased from that of the 3.5 level, but decalcification becomes a definite problem.

EXAMPLE II

Into a container was added 7.5 grams sodium carboxymethylcellulose, 145.0 grams glycerin and 700 grams insoluble sodium metaphosphate. The container was slowly heated to 105° F. accompanied by continuous stirring. 1.5 Grams of xylitol, 2.0 grams spearmint oil flavoring agent and 1.0 gram inert coloring agent were added to the heated gel composition. 2.0 Grams of stannous fluoride and 2.0 grams of sodium dihydrogen phosphate were added during stirring as the container was allowed to cool. This dentifrice composition was in the form of a pleasantly colored blue-green translucent gel and the pH of the composition was about 3.5.

The cooled dentifrice composition was placed in a single tube type dentifrice delivery tube. The dentifrice composition was pleasant to the taste during brushing of the teeth and provided a pleasant aftertaste that remained for several minutes after use.

The insoluble sodium metaphosphate constituent had been previously prepared by tumbling to round the corners and sharp edges of the crystalline form and to render it more light refractive than light reflective.

The dentrifice of Example II was also modified by increased and decreased volumes of sodium dihydrogen phosphate with fluoride penetration results on human extracted teeth further indicating a pH range of between 2 and 5 and preferably about 3.5 being considered optimum from the standpoint of fluoride penetration as opposed to decalcification in the acid environment of the dentifrice.

EXAMPLE III

Into a container was added 7.5 grams sodium caroxymethylcellulose, 145.0 grams glycerin and 700 grams insoluble sodium metaphosphate. The container was slowly heated to a temperature of 105° F. with continuous stirring during heating. 1.5 Grams of xylitol, 2.0 grams cherry flavoring agent and 1.0 gram inert coloring agent were added to the heated gel composition. 2.0 Grams of stannous fluoride, 2.0 grams sodium dihydrogen phosphate and 10.0 grams sodium lauryl sulfate were also added during stirring as the container was allowed to cool. This dentifrice composition was in the form of a red paste of pleasing color. The cooled dentifrice composition was placed into a single compartment type dentifrice delivery tube. During brushing with the dentifrice, the detergent constituent caused a pleasant foaming action to occur. The taste of the dentifrce was pleasing and a pleasant aftertaste remained in the oral cavity for several minutes thereafter.

EXAMPLE IV

A denfifrice composition was prepared incorporating a carrier fluid including 10.0 grams sodium carboxymethylcellulose and 75.0 grams glycerin to which was added 700.0 grams calcium pyrophosphate and 75.0 grams distilled water. These dentifrice constituents were slowly heated in a glass container to a temperature of 105° F. with continuous stirring occurring during heating. 1.5 grams of xylitol, 2.0 grams cherry flavoring and 1.0 grams inert red coloring agent were added to the heated gel-paste composition. 4.0 Grams sodium dihydrogen phosphate and 10.0 grams sodium lauryl sulfate were also added during stirring as the container was allowed to cool. The resulting sodium dihydrogen phosphate dentifrice was in the form of a red paste of pleasing color.

Tests of the dentifrice composition of Example IV were conducted for determination of the activity of sodium dihydrogen phosphate on the enamel of teech without the presence of a fluoride containing compound. Varying amounts of sodium dihydrogen phosphate were incorporated into the basic dentifrice composition of Example IV and the effects of the dentifrice on the enamel of extracted teeth were observed. The tests indicate that the crystalline latticework of the enamel is altered and it is considered that the resulting crystalline form of the enamel is more electrically stable, and thus, the enamel is rendered more resistant to the development of caries.

ACTIVITY OF THE FLUOROPHOSPHATE COMPLEX

As mentioned above, the enamel of the teeth has been shown to define a latticework of minute crystals of hydroxy-apatite. Basically, the enamel latticework is defined by crystalline or prism-like microcrystals of a hydroxy-apatite, which is a form of calcium phosphate. These minute crystals of hydroxy-apatite have various ions associated therewith which complete the electrical stability of the crystal. Also, as mentioned above, application of a dentifrice material to the teeth having an acid pH below a nominal range causes the crystlline latticework of the enamel to open or become activated, thereby preparing the latticework for effective penetration of the fluoride incorporated within the dentifrice.

When the sodium dihydrogen phosphate is applied to the teeth in conjunction with the stannous fluoride compound in the form of a dentifrice, the acid phosphate that is defined by the sodium dihydrogen phosphate opens up or activates the crystal latticework of the enamel and allows the prism-like microcrystals to accept the acid phosphate complex as well as the fluoride into the latticework much more readily than if the dentifrice contained stannous fluoride or sodium fluoride alone. The activity is characteristic of the joining relationship of ions such that the fluoride compound and the phosphate complex is in effect transmitted ionically deeply into the crystalline latticework. In effect, the sodium dihydrogen phosphate opens up the enamel hydroxy-apatite crystal and allows the fluoride phosphate complex to penetrate into the crystal and then pass from that crystal to other hydroxy-apatite crystals of the latticework in the nature of a chain reaction. Thus, there is provided a significantly deeper penetration of the fluoride compound when utilized in conjunction with the sodium dihydrogen phosphate than is ordinarily available through use of the fluoride compound alone.

Through use of a dentifrice containing stannous fluoride and sodium dihydrogen phosphate within an appropriate pH range, there is provided a fluorophosphate hydroxy-apatite crystal that is electrically stable. The stannous fluoride or tin fluoride that is in the compound will then combine with the surface layer of the enamel and will cause a complete crystalline change at the surface of the enamel. This crystalline change, i.e. from a monoclinic prism-like configuration to a rhomboid shape, that is effected by the stannous fluoride develops a sealing or capping effect at the enamel surface and this sealing or capping effect effectively retards leaching of the fluorophosphate complex from the hydroxy-apatite latticework. In effect, when sodium dihydrogen phosphate is utilized in conjunction with a tin or stannous fluoride, a much greater penetration of the fluoride and the phosphate into the enamel crystalline latticework is developed as compared with the fluoride penetration or acid phosphate penetration when stannous fluoride and sodium dihydrogen phosphate are utilized alone. The stannous or tin portion of the compound then combines with the surface to provide a sealing or capping effect, to prevent the fluorophosphate from being rapidly leached back out of the enamel latticework.

It should be noted that the sealing or capping effect established by the stannous fluoride complex is strictly a surface phenomenon. After the tin is worn away from the surface of the enamel crystalline latticework, the fluorophosphate complex then is capable of being leached out of the enamel latticework by the natural activities of the fluids contained within the oral environment. When fluoride containing dentifrice materials are utilized at the rather weak solution level allowed by governmental authority, even with the elevated degree of phosphate and fluoride penetration promoted by sodium dihydrogen phosphate enhancement, much of the fluoride can be leached out of the crystalline enamel latticework within a short period of time. By providing a stannous fluoride containing dentifrice and with the caries resistance activities promoted by the stannous fluoride being enhanced by the sodium dihydrogen phosphate, enhanced fluorophosphate treatment can be effected on a daily basis. Such daily fluorophosphate treatment provides the enamel crystalline latticework with greater fluorophosphate penetration into the enamel and retarded leaching of the fluorophosphate from the crystalline latticework on a daily basis. Moreover, on a daily basis the enamel surface is capped or sealed with a new microlayer of tin, thereby promoting effective retention of the fluorophosphate complex within the tooth structure and thus effectively promoting continuing resistance to the development of caries.

It has been determined through tests that penetration of various other fluoride containing compounds is rendered more effective through the use of various other acid phosphate compounds and particularly sodium dihydrogen phosphate. Thus, when a dentifrice containing sodium fluoride is utilized rather than stannous fluoride in conjunction with sodium dihydrogen phosphate, for example, the result is an enhanced or increased penetration of the phosphate fluoride into the enamel latticework much more effectively than if the sodium fluoride were utilized alone in the dentifrice composition. Sodium dihydrogen phosphate has been found imminently more effective than any other acid phosphate because the sodium dihydrogen phosphate has the unusual characteristic of altering the crystalline latticework of the enamel, allowing the fluoride compound to penetrate more deeply into the crystalline latticework of the enamel. Although other acid phosphate compounds enhance penetration of other fluoride containing compounds to some limited degree, utilization of sodium dihydrogen phosphate as the acid phosphate compound has been found to be infinitely more effective. Sodium dihydrogen phosphate has the characteristic of being able to force the fluoride much more deeply into the crystalline latticework of the enamel because of the chain reaction that occurs between the ions in the enamel crystal.

Unfortunately, the sodium fluoride does not provide a capping or sealing effect at the enamel surface and therefore there is no surface sealing phenomenon to retard natural oral fluid leaching of the fluorophosphate complex from the enamel latticework. Even though the teeth are brushed with a dentifrice containing sodium fluoride and sodium dihydrogen phosphate so that excellent penetration of the fluorophosphate is obtained, the lack of a capping of sealing activity such as occurs when stannous fluoride is employed will allow the fluorophosphate to very quickly be leached out of the enamel material, thereby rendering the enamel susceptible to caries activity.

Sodium dihydrogen phosphate by itself when used solely as the caries inhibiting compound without any fluoride demonstrates more effective caries resistance potential than either stannous fluoride, sodium fluoride or sodium monofluorophosphate used alone or in combination with other acid phosphate compounds. It is theorized that the sodium dihydrogen phosphate within an acid pH between 2.0 and 5.0 and optimally at 3.5 causes the enamel or hydroxy-apatite crystal to be structurally modified to a crystalline form that is more electrically stabilized and thus more resistant to decalcification or crystalline breakdown. It is further theorized that certain electrically unstable ions within the crystalline latticework, such as carbonate ions, are displaced and replaced by the more electrically stable phosphate and acid phosphate ions. The resulting crystalline network is thus changed to a more electrically stable form that is effectively resistant to the development of caries.

The tin or stannous fluoride, when utilized in conjunction with sodium dihydrogen phosphate, enhances the stability of the fluorophosphate within the hydroxy-apatite crystal. For this reason, it is preferred to utilize stannous fluoride in conjunction with sodium dihydrogen phosphate rather than to rely on the limited mechanism of activity provided by various fluoride containing compounds other than stannous fluoride.

The acid pH range that is established by appropriate combination of sodium dihydrogen phosphate and stannous fluoride renders the ions within the hydroxy-apatite crystal latticework more active. The acid pH creates an effect that is somewhat like introducing heat in a chemical reaction for the purpose of speeding up the reaction. By providing an acid environment, the enamel latticework is activated so that the fluoride and phosphate reacts with the enamel in a much more rapid fashion. If the pH of the composition were basic, the hydroxy-apatite crystalline latticework will remain inactive and will, in effect, remain substantially sealed, thus retarding penetration of the fluoride into the enamel material. Tests indicate that penetration of the fluoride into the enamel will be minimal when the pH is basic. The dentifrice materials that are currently sold to the public typically employ a neutral or slightly acid environment, but the more basic pH levels of the dentifrice materials provide minimal enamel surface activities or reaction that enhance penetration of the fluoride complex into the crystalline latticework of the enamel.

The pH of the dentifrice composition of the present invention is, relatively speaking, a more acid pH than exists in other dentifrice compositions that are available to the public. The pH range of this dentifrice composition is in the range of between 2 and 5 and preferably about 3.5. This particular range is more acid that any other presently available dentifrice. A dentifrice material that is very acid, such as in the pH range of 2 or 3, is vastly different as compared to a material having a pH in the range of 5 to 7, which is, of course, only slightly acid. The pH that is involved with the present invention is the ideal or optimum range for the mechanism of action of the sodium dihydrogen phosphate in combination with stannous fluoride for the purpose of achieving optimum penetration of the fluoride and phosphate compound into the enamel.

Some of the acid phosphate prophylactic gels are pastes that are used in dental offices and are quite effective, have a pH in the range of from 4-4.5. These prophylactic gels and pastes, however, as far as the anticaries activity is concerned, are well below the anticaries activity that is developed when sodium dihydrogen phosphate by itself or in conjunction with stannous fluoride is used. Sodium dihydrogen phosphate is the only acid phosphate that effectively enhances the penetration of all fluorides. All of the other phosphate compounds at some point interfere with the mechanism of fluoride compounds. For some reason that is surprising and not fully understood, only sodium dihydrogen phosphate enables the deep ion penetration characteristics that facilitate enhanced anticaries activity as compared to combinations of other fluoride and phosphate compounds.

Tests are conducted utilizing sodium monohydrogen phosphate in order to determine possible penetration and anticaries treatment of teeth. It was determined without question that the sodium monohydrogen phosphate does not function nearly as well as the sodium dihydrogen phosphate. The sodium dihydrogen phosphate, when used at varying pH levels, was demonstrated to have optimum penetration without noticeable decalcification at a pH of about 3.5. As the pH of the dentifrice material becomes more basic, the mechanism of penetration activity is obviously less operative. In the pH range of about 5, penetration activity is nominal. As the pH of the dentifrice material becomes more acid as compared to the optimum pH of about 3.5, the penetration activity of the fluoride seems to increase slightly as compared to penetration at a pH of about 3.5. However, as the dentifrice material becomes more acid in character, the pH actually becomes a problem rather than an enhancement. At a pH of 2 or lower, decalcification of the enamel of the teeth proceeds rather rapidly so that the benefit of the phosphate or the fluoride versus decalcification becomes moot.

The sodium or potassium acid phosphates seem to work well from the standpoint of penetration but, as compared to the penetration obtained by sodium dihydrogen phosphate with fluoride enhancement, the other acid phosphate compounds achieve only nominal ion penetration. As a matter of fact, the sodium dihydrogen phosphate is so superior in fluoride penetration enhancement as compared to the other acid phosphate materials such as sodium or potassium acid phosphate, that it is hardly fair to compare them from the standpoint of effectiveness. This is in distinct contrast, however, with the phosphoric acids, such as orthophosphoric acid, which is currently being used in some fluoride phosphate gel type prophylactic preparations for restricted use only in dental offices. These materials are definitely acid in character and they are not nearly as effective as sodium dihydrogen phosphate from the standpoint of fluoride penetration enhancement. Acid phosphate materials cover a wide range of materials but, at the present time, only sodium dihydrogen phosphate has been found to have these exceptional characteristics from the standpoint of fluoride penetration enhancement.

An interesting phenomenon concerned with the employment of sodium dihydrogen phosphate in combination with stannous fluoride is the capping effect or surface phenomenon that occurs particularly with stannous fluoride and which does not occur when other fluoride compounds are employed. When sodium dihydrogen phosphate is employed in conjunction with stannous fluoride, there is obtained an imminently greater penetration than is obtained when other phosphate compounds are employed and then a capping or surface sealing effect occurs because of the particular pH of the composition. A low pH, optimally around 3.5, yields an effective penetration of the sodium dihydrogen phosphate fluorocomplex into or through the enamel latticework of the teeth. The particular chemical activity that occurs is that the fluoride replaces hydroxyl or OH ions. The pH of the composition is raised to the point where stannous fluoride then functions at the surface of the enamel to provide the surface phenomenon and then caps off or seals the enamel. If the pH of the composition is lowered to around a pH of 2, effective penetration of the enamel structure will occur but the capping or sealing effect caused by the tin becomes inneffective. The reason for this activity is that only so much fluoride penetration can occur, before calcium, carbonate or hydroxyl ion are released and decalcification or complete crystalline breakdown becomes a significant factor. If an excessive amount of calcium is released in the chemical activity, the enamel structure of the tooth is effectively being dissolved which, of course, is an undesirable phenomenon. So the reason for the mechanism of action of the sodium dihydrogen phosphate with stannous fluoride at an optimum pH range of about 3.5 is that the pH that allows for the penetration of the acid fluorophosphate complex within the enamel latticework. As soon as the pH on a microscopic level is raised to the point where stannous fluoride is effective and the crystals become electrically stable, then the capping or sealing effect becomes predominant and, in effect, a degree of fluoride penetration is prevented by the capping or sealing effect accomplished by the stannous fluoride.

When sodium fluoride is utilized in conjunction with sodium dihydrogen phosphate in an acid environment, there is yielded effective fluoride penetration but there is no sealing and capping effect developed as occurs with stannous fluoride. As soon as the mechanism of action is ceased and the pH environment is changed, such as when the oral environment is rinsed after brushing, the fluorophosphate complex begins to be leached out of the tooth purely by the law of mass action. There occurs, therefore, a release of the fluoride mechanism in the absence of the capping effect offered by stannous fluoride and therefore the overall fluoride treatment and caries resistance is considered more ineffective as compared with that obtained by stannous fluoride and sodium dihydrogen phosphate.

Since stannous fluoride is the preferred fluoride to use in conjunction with sodium dihydrogen phosphate and since stannous fluoride is unstable for long periods of time, such as would be necessary for storage in a tube on a shelf, in an aqueous medium, the combination of stannous fluoride with sodium dihydrogen phosphate in a nonreactive water-free carrier is necessary for practical storage and shelf life. The reason for the water-free carrier is to prevent the degradation of the stannous fluoride component and not the sodium dihydrogen phosphate part.

In view of the foregoing, it is clear that the dentifrice composition of the present invention provides all of the features and improvements indicated hereinabove together with other features that are inherent from this disclosure. The invention may also take other forms within the spirit and scope of the appended claims:

What is claimed is:

1. A fluoride containing dentifrice composition having an acid phosphate enhanced fluoride system that penetrates and alters tooth enamel and is retained well in the enamel crystal latticework, said dentifrice being comprised of:
   a water free carrier;
   a quantity of an abrasive material from a group including insoluble sodium metaphosphate, dicalcium phosphate dihydrite and insoluble calcium pyrophosphate;
   a quantity of sweetening agent from a group consisting essentially of xylitol, sugar and sacharrin;
   a flavoring agent from a group consisting essentially of spearmint oil, citrus oils, fruit oils, vanilla oil, chocolate, grape and cinnamon;
   a quantity of stannous fluoride, said stannous fluoride compound being in the range of from 0.03% to 0.4% by weight of said dentifrice composition; and
   a quantity of sodium dihydrogen phosphate being incorporated within said carrier and adjusting the pH of the dentifrice composition to an acid range from about 2.5 to about 5.5 said sodium dihydrogen phosphate comprising from about 0.03% to about 0.4% by weight of said dentifrice composition and being capable of altering the crystalline latticework structure of tooth enamel during a toothbrushing sequence and reacting together with said stannous fluoride and providing a caries inhibiting fluorophosphate complex at the tooth surface energized by said sodium dihydrogen phosphate.

2. A fluoride and acid phosphate containing dentifrice composition as recited in claim 1, wherein:
   said acid phosphate adjusts the pH of said dentifrice composition to about 3.5.

3. A fluoride and acid phosphate containing dentifrice composition as recited in claim 1, wherein:
   the ratios of said fluoride containing compound and said acid phosphate in said dentifrice compound are of substantially equal proportion by weight.

4. A fluoride and acid phosphate containing dentifrice composition as recited in claim 1, wherein:
   said stannous fluoride comprises about 0.4% of said dentifrice composition by weight; and
   said sodium dihydrogen phosphate comprises about 0.4% of said dentifrice composition by weight.

5. A fluoride and acid phosphate containing dentifrice as recited in claim 1, wherein said carrier is a water free gel carrier comprising:
   a quantity of glycerin in the range of from about 5% to about 50% of said dentifrice composition by weight; and
   a quantity of carboxymethylcellulose in the range of from about 10% to about 75% of said dentifrice composition by weight.

6. In a dentifrice composition that is acceptable for daily use in the maintenance of oral hygiene and which incorporates a water-free carrier, abrasive material, sweetening agent, flavoring agent and a foaming agent, the improvement comprising:
   a quantity of stannous fluoride having a fluoride concentration in the range of from about 0.03% to 0.4% by weight of said dentifrice composition; and
   a quantity of sodium dihydrogen phosphate sufficient to adjust the pH of said dentifrice composition to a pH range of between 2.5 and 5, said sodium dihydrogen phosphate and stannous fluoride reacting with the enamel of the teeth during a tooth brushing sequence to activate the crystalline latticework of the enamel and promote enhanced penetration of the fluoride into the enamel, thus developing a caries inhibiting fluorophosphate complex within the crystalline latticework of the tooth enamel.

7. The improvement of claim 6, wherein said dentifrice composition includes:
   stannous fluoride and sodium dihydrogen phosphate within a predetermined pH range that is sufficient to induce tin microsealing of the enamel surface after penetration of the fluoride and sodium dihydrogen phosphate into the crystalline latticework of the enamel.

8. In a dentifrice composition that is acceptable for daily use in the maintenance of oral hygiene and which incorporates a carrier agent incorporating an abrasive material, sweetening agent, flavoring agent and a foaming agent, the improvement comprising:
   a quantity of sodium dihydrogen phosphate being incorporated into said dentifrice composition in sufficient amount to adjust the pH of said dentifrice composition to a pH range of from about 2.0 to about 5, said sodium dihydrogen phosphate reacting with the enamel of the teeth during a toothbrushing sequence to modify the crystalline latticework of the enamel to render it resistant to the development of the caries.

* * * * *